United States Patent
Van Lier

(10) Patent No.: US 8,872,974 B2
(45) Date of Patent: Oct. 28, 2014

(54) METHOD AND SYSTEM FOR AVOIDING DISCOMFORT AND/OR RELIEVING MOTION SICKNESS WHEN USING A DISPLAY DEVICE IN A MOVING ENVIRONMENT

(75) Inventor: Jan Van Lier, Korntal-Muenchingen (DE)

(73) Assignee: Alcatel Lucent, Boulogne-Billancourt (FR)

( * ) Notice: Subject to any disclaimer, the term of this patent is extended or adjusted under 35 U.S.C. 154(b) by 0 days.

(21) Appl. No.: 13/982,505

(22) PCT Filed: Mar. 23, 2012

(86) PCT No.: PCT/EP2012/055164
§ 371 (c)(1),
(2), (4) Date: Oct. 3, 2013

(87) PCT Pub. No.: WO2012/130741
PCT Pub. Date: Oct. 4, 2012

(65) Prior Publication Data
US 2014/0036153 A1    Feb. 6, 2014

(30) Foreign Application Priority Data

Mar. 31, 2011 (EP) .................................. 11290163

(51) Int. Cl.
*H04N 5/445* (2011.01)
*H04N 5/262* (2006.01)
*G09G 5/00* (2006.01)
*A61M 21/00* (2006.01)

(52) U.S. Cl.
CPC .......... *H04N 5/262* (2013.01); *G09G 2340/14* (2013.01); *A61M 2205/332* (2013.01); *G09G 2354/00* (2013.01); *A61M 2021/005* (2013.01); *G09G 2380/00* (2013.01); *A61M 2021/0011* (2013.01); *A61M 21/00* (2013.01); *G09G 5/00* (2013.01)
USPC .............. 348/563; 348/589; 345/632; 600/27

(58) Field of Classification Search
CPC .................. H04N 9/74; H04N 5/445–5/44591
USPC .................... 348/563, 584–589, 706; 600/27; 345/632–633
See application file for complete search history.

(56) References Cited

U.S. PATENT DOCUMENTS 4,616,261 A * 10/1986 Crawford et al. ............. 348/563
2002/0099257 A1 * 7/2002 Parker et al. .................... 600/27
(Continued)

FOREIGN PATENT DOCUMENTS

EP    1977931 A1    10/2008
EP    2228089       9/2010
(Continued)

OTHER PUBLICATIONS

Karremans, J. et al. "Beyond Vicary's Fantasies: The Impact of Subliminal Priming and Brand Choice" Journal of Experimental Social Psychology vol. 42, 2006, pp. 792-798.
(Continued)

*Primary Examiner* — Michael Lee
(74) *Attorney, Agent, or Firm* — Harness, Dickey & Pierce

(57) ABSTRACT

In one embodiment, a method for avoiding discomfort and/or relieving motion sickness when using a display device in a moving environment includes detecting at least one movement component of the moving environment, generating data for intermediate images indicating the movement component or at least one of the movement components, and modifying a series of images showing content to be displayed by inserting the intermediate images into the series. The modified series is divided into sequences of these images by the intermediate images. The method further includes displaying the modified series of images on an image display of the display device. The modified series includes the intermediate images.

15 Claims, 2 Drawing Sheets

(56) References Cited

U.S. PATENT DOCUMENTS

Figure 1:
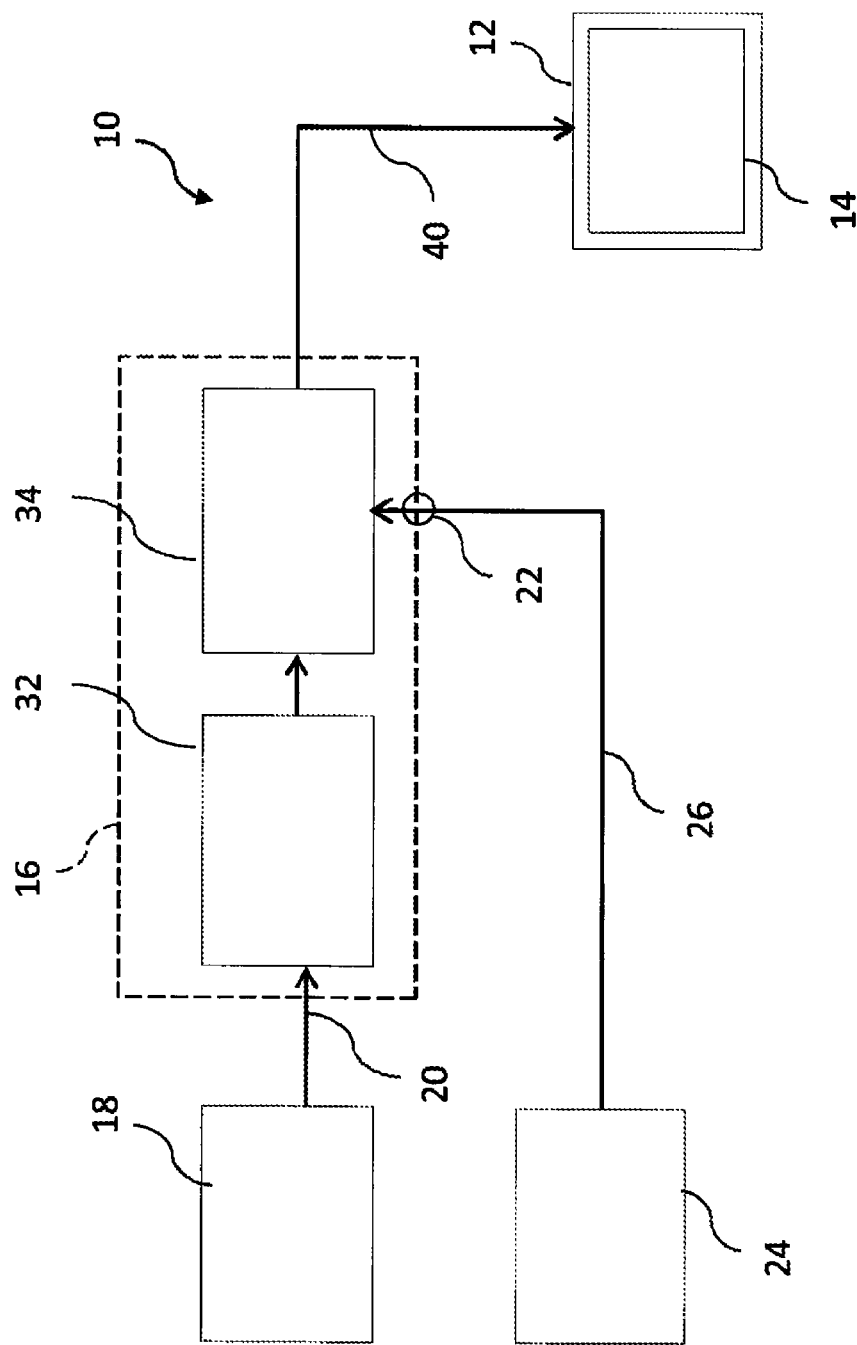

2006/0079729 A1 4/2006 Kim
2008/0062008 A1 3/2008 Morimoto et al.

FOREIGN PATENT DOCUMENTS

EP 2228089 A1 9/2010
TW 200940116 10/2009
WO WO 2004/047711 6/2004

OTHER PUBLICATIONS

International Search Report PCT/ISA/210 for International Application No. PCT/EP2012/055164 Dated May 7, 2012.

Written Opinion of the International Searching Authority PCT/ISA/237 for International Application No. PCT/EP2012/055164.

Jul. 25, 2014 Taiwanese Office Action issued in TW Application 101111573 (translation).

* cited by examiner

METHOD AND SYSTEM FOR AVOIDING DISCOMFORT AND/OR RELIEVING MOTION SICKNESS WHEN USING A DISPLAY DEVICE IN A MOVING ENVIRONMENT

This application is the national phase under 35 U.S.C. §371 of PCT International Application No. PCT/EP2012/055164 which has an International filing date of Mar. 23, 2012, which claims priority to European patent application number EP 11290163.2 filed Mar. 31, 2011; the entire contents of each of which are hereby encorporated by reference.

The present invention relates to a method for avoiding discomfort and/or relieving motion sickness when using a display device in a moving environment. The invention further relates to a corresponding image-processing device and a corresponding system comprising the image-processing device.

There are already approaches for relieving motion sickness or other discomforts caused by the use of display devices in a moving environment. These approaches are concentrating on the discrepancy between visual information and equilibrium sense.

The patent application EP 1 977 931 A1 shows an image display device for installation in a vehicle which is capable of reducing the occurrence of motion sickness by detecting the behaviour of the vehicle and transforming the images to be displayed.

It is an object of the invention to provide an alternative method and device for avoiding discomfort and/or relieving motion sickness caused by the discrepancy between visual information and equilibrium sense.

This object is achieved by the independent claims. The dependent claims detail advantageous embodiments of the invention.

The method according to the invention comprises the following steps: Detecting at least one movement component of the moving environment. Generating data for intermediate images, which intermediate images indicate the movement component or at least one of the movement components. Modifying a series of images showing the content to be displayed by inserting the intermediate images into the series of images, wherein the series is divided into sequences of a plurality of these images by the intermediate images. Displaying the modified series of images on an image display of the display device, wherein the modified series includes the intermediate images.

The basic idea of this invention is to combine the detection of movement of the moving environment of the display device with the concept of subliminal messages known from subliminal advertisement so that the displayed content seems to be unchanged but hidden visual information is inserted which is sensed by the subconscious mind creating consistency with the equilibrium sense.

Subliminal effects where discussed very controversially since they were topic of a faked psychological experiment in 1957. The authors stated that replacing one of the 24 pictures per second of a movie by an advertisement message drastically influences the sales figure of the advertised product. More research that is recent has proven that in fact people can be influenced by this subliminal manipulation method. However, the preference of a certain product can only be amplified if there is a physical need and so the advert is goal-relevant. For example, the preference for a special drink can be amplified if the viewer is thirsty but it does not influence the viewer if he is not thirsty. (Reference: Karremans, J.; Stroebe, W.; Claus, J. "Beyond Vicary's fantasies: The impact of subliminal priming and brand choice"; Journal of Experimental Social Psychology 42: p. 792-798; 2006).

According to the invention, the hidden visual information is information indicating the movement component or at least one of the movement components of the detected movement. By this information, the subconscious mind gets visual information being consistent with the information given by the equilibrium sense. The intermediate images comprising this hidden visual information are presented in such short teams, that it does not interfere the conscious perception of the content to be displayed. The content will reach the consciousness of a person looking at the image display, wherein the subconscious mind of the person will sense the additional visual information. This will relieve motion sickness or at least avoid discomfort when using a display device in a moving environment.

According to a preferred embodiment of the present invention, the at least one movement component is a velocity and/or an acceleration and/or an angular velocity and/or an angular acceleration.

According to another preferred embodiment of the present invention, the at least one movement component or at least one of the movement components is a movement component in a direction within a plane parallel to the screen plane of the image display. Additionally or alternatively the at least one movement component or at least one of the movement components is a movement component in a direction perpendicular to the screen plane of the image display.

According to another preferred embodiment of the present invention, the intermediate images show at least one reference structure optically indicating the movement of the display device. By the hidden visual information of a moving reference structure, the subconscious mind of a person looking at the image display gets visual information being consistent with the information given by the equilibrium sense of this person.

According to yet another preferred embodiment of the present invention, the succession of intermediate images generates motion pictures (a film). These motion pictures could show some arrangement of structures being rectangular frames or circles, which are centred to the image display if the motion of the display device is constant and get bigger with time like lines in a tunnel, which is passed until they leave the image display. New structures like frames occur in the centre of the display (as this virtual tunnel does not end). Each detected acceleration leads to a change in these (real time) motion pictures. Lateral changes (i.e. change of velocity) just change the speed of the frame growth whereas transversal ones e.g. in curves lead to a deviation of the frames from the centre of the display. This deviation is low for the big frames (appear near to the viewer) and is getting more pronounced for smaller frames and is maximum for the newly appearing frames generating a curve in the virtual tunnel. Another possibility of motion pictures could be for example a virtual rollercoaster tour matching to the sensed motion information.

According to yet another preferred embodiment of the present invention, the detecting is performed by means of at least one sensor, which sensor(s) is/are at least one velocity sensor and/or at least one acceleration sensor and/or at least one angular velocity sensor and/or at least one angular acceleration sensor.

The invention further relates to a computer-readable medium such as a storage device, a floppy disk, CD, DVD, Blue Ray disk, or a random access memory (RAM), containing a set of instruction that causes a computer to perform an aforementioned method and a computer program product comprising a computer usable medium including computer usable program code, wherein the computer usable program code is adapted to execute the aforementioned method.

The present invention further refers to an image-processing device for generating image data of images to be displayed on an image display of a display device in a moving environment. Said image-processing device is arranged for generating data of intermediate images, which intermediate images indicate the movement or at least one of the movement components of the moving environment. The image-processing device is further arranged for inserting the intermediate images into a series of images showing content to be displayed, wherein the series is divided into sequences of these images by the intermediate images. This image-processing device can be called a "motion thickness relief device" or "motion thickness relief module". The inserting of an intermediate image can be a replacement of an oriainal image, a superimposion of the intermediate image with the original image or an addition of an intermediate image to original images.

The present invention further refers to a system for displaying images in a moving environment. This system is preferably a device like for example a laptop computer. The system comprises a display device with an image display for displaying the images, at least one sensor for detecting the movement or at least one movement component of the moving environment and an aforementioned image-processing device connected to the display device and to the sensor by sitmal connections. The moving environment is for example a moving ship, plane or vehicle like a car or commercial vehicle. The movement component or movement components especially is/are the movement component(s) of the display device itself.

As today's display devices have a high display frequency oversampling the input signal it seems to be preferable to have the image-processing device (motion thickness relief module) integrated into the display device.

Preferably, the system is arranged for performing the aforementioned method for displaying images.

According to a preferred embodiment of the present invention, the sensor is a velocity sensor, an acceleration sensor and/or an angular velocity sensor and/or an angular acceleration sensor. Accordingly, the detection of a movement component can go beyond the detection of a velocity or velocity component.

Aspects of the present invention are described below with reference to flowchart illustrations and/or block diagrams of methods, devices (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

These and other aspects of the invention will be apparent from and elucidated with reference to the embodiments described hereinafter.

Figure 2:
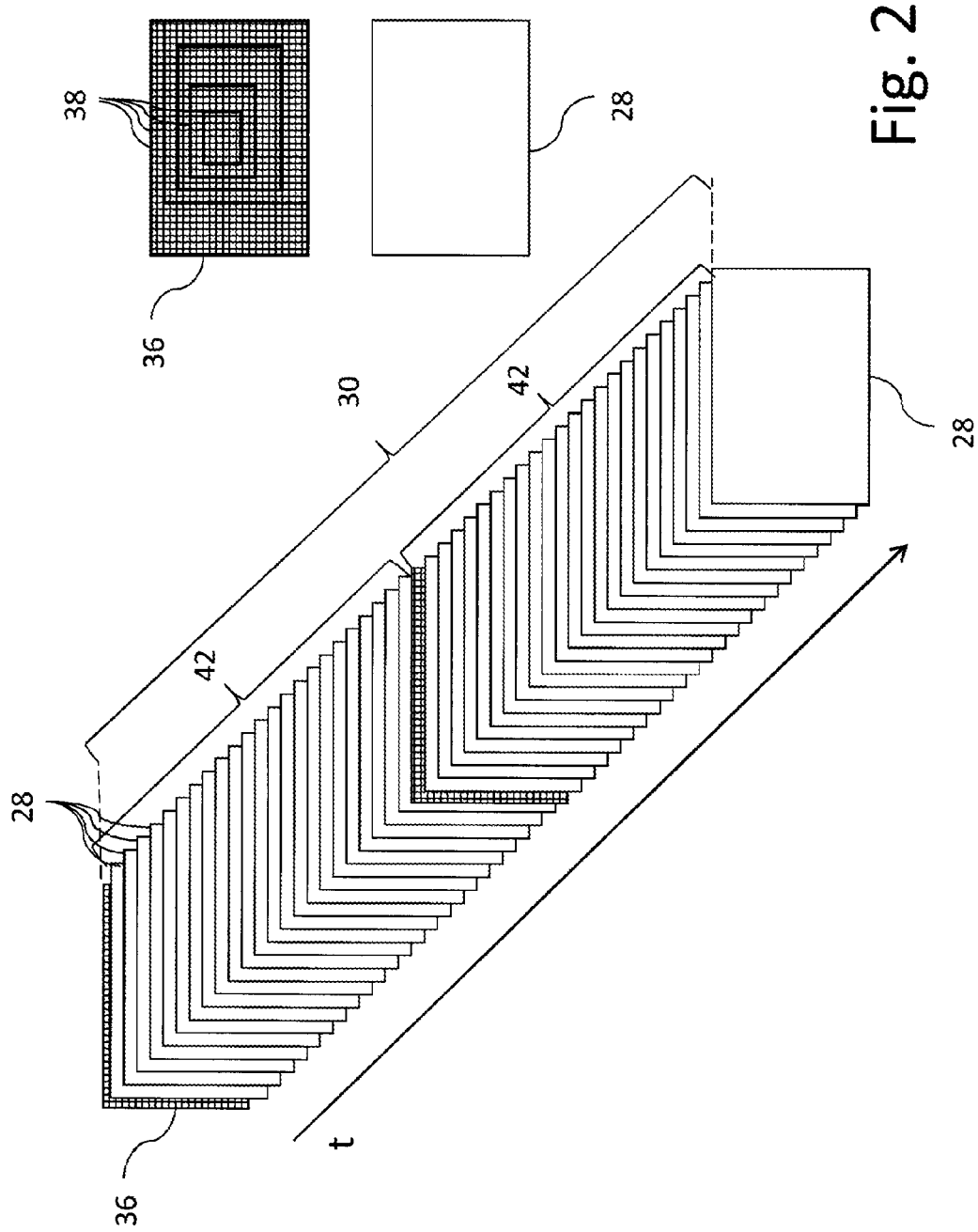

In the drawings:

FIG. 1 depicts a schematic representation of a system/device according to a preferred embodiment of the invention and FIG. 2 depicts a schematic representation of a series of images being divided into sequences of these images by intermediate images.

FIG. 1 depicts a system 10 comprising a display device 12 with an image display (screen) 14 for displaying images. The system further comprises an image-processing device 16 for generating image data of the images to be displayed on the image display 14. The image-processing device 16 is connected to a sensor 18 or a plurality of sensors 18 by a signal connection 20. The sensors 18 are sensors 18 for detecting the movement (or at least movement components) of an environment of the display device 12. The image-processing device 16 further comprises an interface 22 for connecting the image-processing device 16 to a device 24 by means of another signal connection 26. The device 24 supplies data to the system 10, which data comprise the content to be displayed on the image display 14. In other words, these data are image data of a series of images 28 showing the content to be displayed. A modified series 30 based on this series of images 28 is shown in FIG. 2.

The image-processing device 16 comprises at least two functional units 32, 34. The first functional unit 32 generates the data of intermediate images 36 (shown in FIG. 2 as well). The succession of these intermediate images 36 are motion pictures of reference structures 38 indicating the detected movement. Therefore, this unit is a unit 32 for generating motion pictures. The second functional unit 34 is a unit for generating the modified series 30 of images 28, 32 including the intermediate images 36. The processing device 16 is connected to the display device 12 by another signal connection 40.

The modified series 30 of images depicted in FIG. 2 is divided into sequences 42, each consisting of twenty-four images 28, 36. One of the images 28, 36 is the intermediate image 36, the other following twenty-three images are the images 28 showing the content to be displayed. The images 28, 36 of this modified series 30 are displayed on the image display 14 in a time series indicated by the arrow labeled t. Optional the intermediate image 36 replaces one of the original twenty-four images 28 per second or superimposes this image 28.

The intermediate images 36 show reference structures 36 optically indicating the movement of the environment and the display device 12. The succession of intermediate images 36 within the modified series 30 of images 28, 36 generates motion pictures of the reference structures 38. These motion pictures are an arrangement of rectangular frames 38, which get bigger with time like lines in a tunnel, which is passed, wherein each structure 38 starts as a point at the centre of the image display 14 and seems to leave the image display 14 after a while.

By this information, the subconscious mind gets visual information being consistent with the information given by the equilibrium sense. The intermediate images 36 comprising this hidden visual information are presented in such short terms, that it does not interfere the conscious perception of the content to be displayed. The content will reach the consciousness of a person looking at the image display 14, wherein the subconscious mind of the person will sense the additional visual information. This will relieve motion sickness or at least avoid discomfort when using a display device 12 in a moving environment.

The corresponding approach for avoiding discomfort and/or relieving motion sickness when using a display device in a moving environment comprises the following steps:
(i) detecting at least one movement component of the moving environment;
(ii) generating data for intermediate images 36 indicating the movement component or at least one of the movement components;
(iii) modifying a series of images 28 showing content to be displayed by inserting the intermediate images 36 into the series of images 28, wherein the series is divided into sequences 42 of a plurality of these images by the intermediate images 36; and
(iv) displaying the modified series of images 30 on an image display 14 of the display device 12, wherein the modified series 30 includes the inserted intermediate images 36.

While the invention has been illustrated and described in detail in the drawings and foregoing description, such illustration and description are to be considered illustrative or exemplary and not restrictive; the invention is not limited to the disclosed embodiments.

Other variations to be disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting scope.

The invention claimed is:

1. A method for avoiding discomfort and/or relieving motion sickness when using a display device in a moving environment, the method comprising the steps:
   detecting at least one movement component of the moving environment;
   generating data for intermediate images indicating the movement component or at least one of the movement components;
   modifying a series of images showing content to be displayed by inserting the intermediate images into the series, wherein the series is divided into sequences of these images by the intermediate images; and
   displaying the modified series of images on an image display of the display device, wherein the modified series includes the intermediate images,
   wherein at least one of the intermediate images is hidden visual information for the subconscious mind of a person viewing the modified series of images, the hidden visual information being consistent with an equilibrium sense of the person.

2. The method according to claim 1, wherein the at least one movement component is a velocity and/or an acceleration and/or an angular velocity and/or an angular acceleration.

3. The method according to claim 1, wherein the at least one movement component or at least one of the movement components is a movement component in a direction within a plane parallel to the screen plane of the image display.

4. The method according claim 1, wherein the at least one movement component or one of the movement components is a movement component in a direction perpendicular to the screen plane of the image display.

5. The method according to claim 1, wherein the intermediate images show at least one reference structure optically indicating the movement of the display device.

6. The method according to claim 5, wherein the succession of intermediate images within the modified series of images generates motion pictures of the reference structure.

7. The method according claim 1, wherein the detecting is performed by means of at least one sensor for measuring the velocity and/or the acceleration and/or the angular velocity of the display device.

8. A non-transitory computer-readable medium including at least one of a storage device, a floppy disk, CD, DVD, Blue Ray disk, or a random access memory (RAM), containing a set of instruction that causes a computer to perform a method according to claim 1.

9. A non-transitory computer program product comprising a computer usable medium including computer usable program code, wherein the computer usable program code is adapted to execute the method of claim 1.

10. An image-processing device for generating image data of images to be displayed on an image display of a display device in a moving environment,
   wherein the image-processing device is arranged for generating data of intermediate images, which intermediate images indicate the movement or at least one of the movement components of the moving environment and for modifying the series of images by inserting the intermediate images into a series of images showing content to be displayed,
   wherein the series is divided into sequences of these images by the intermediate images
   wherein at least one of the intermediate images is hidden visual information for the subconscious mind of a person viewing the modified series of images, the hidden visual information being consistent with an equilibrium sense of the person.

11. A system, preferably a device, for displaying images in a moving environment, the system comprising: a display device with an image display for displaying the images, at least one sensor for detecting the movement or at least one movement component of the moving environment and an image-processing device according to claim 10 connected to the display device and to the sensor by signal connections.

12. The system according to claim 11, wherein the system is arranged for performing the method of one of the preceding method claims.

13. The system according to claim 11, wherein the sensor is a velocity sensor, an acceleration sensor, an angular velocity sensor and/or an angular acceleration sensor.

14. The method of claim 1, wherein the intermediate images are not displayed at a same instant in time as the images showing content.

15. The system of claim 11, wherein the intermediate images are not displayed at a same instant in time as the images showing content.

* * * * *